United States Patent
Maddinelli et al.

(10) Patent No.: US 9,367,796 B2
(45) Date of Patent: Jun. 14, 2016

(54) METHOD FOR PREDICTING THE PROPERTIES OF CRUDE OILS BY THE APPLICATION OF NEURAL NETWORKS

(71) Applicant: Eni S.p.A., Rome (IT)

(72) Inventors: Giuseppe Maddinelli, Milan (IT); Silvia Pavoni, Pioltello (IT)

(73) Assignee: ENI S.P.A. (IT)

( * ) Notice: Subject to any disclaimer, the term of this patent is extended or adjusted under 35 U.S.C. 154(b) by 215 days.

(21) Appl. No.: 13/655,214

(22) Filed: Oct. 18, 2012

(65) Prior Publication Data

US 2013/0103627 A1   Apr. 25, 2013

(30) Foreign Application Priority Data

Oct. 21, 2011   (IT) .............................. MI2011A1908

(51) Int. Cl.
*G06N 3/02* (2006.01)
*G01N 24/08* (2006.01)
*G01R 33/44* (2006.01)

(52) U.S. Cl.
CPC ................ *G06N 3/02* (2013.01); *G01N 24/081* (2013.01); *G01R 33/448* (2013.01)

(58) Field of Classification Search
CPC ....... G06N 3/02; G01R 33/448; G01N 24/081
USPC .......................................................... 706/21
See application file for complete search history.

(56) References Cited

U.S. PATENT DOCUMENTS

| | | | | |
|---|---|---|---|---|
| 7,176,682 B2* | 2/2007 | Galford | ................... | G01N 24/08 324/300 |
| 2003/0128032 A1* | 7/2003 | Heaton | ..................... | G01V 3/32 324/303 |
| 2007/0013911 A1* | 1/2007 | DiFoggio | ................... | G01J 3/26 356/436 |

(Continued)

OTHER PUBLICATIONS

Ramos P. et al., "Low field 1H NMR relaxometry and multivariate data analysis in crude oil viscosity predietion", Chemometrics and Intelligent Laboratory Systems, 99, 2009, pp. 121-126.*

(Continued)

*Primary Examiner* — Stanley K Hill
*Assistant Examiner* — Dave Misir
(74) *Attorney, Agent, or Firm* — Tarolli, Sundheim, Covell & Tummino LLP

(57) ABSTRACT

A method for predicting the properties of crude oils by the application of neural networks articulated in phases and characterized by determining the T2 NMR relaxation curve of an unknown crude oil and converting it to a logarithmic relaxation curve; selecting the values of the logarithmic relaxation curve lying on a characterization grid; entering the selected values as input data for a multilayer neural network of the back propagation type, trained and optimized by means of genetic algorithms; predicting, by means of the trained and optimized neural network, the physico-chemical factors of the unknown crude oil.

The method comprises a training and optimization process of the multilayer neural network of the back propagation type. The method thus defined allows the most representative physico-chemical factors of crude oils to be predicted rapidly and without onerous laboratory structures, or alternatively the distillation curve of crude oils with an acceptable approximation degree.

7 Claims, 5 Drawing Sheets

(56) References Cited

U.S. PATENT DOCUMENTS

| | | | | |
|---|---|---|---|---|
| 2008/0253426 A1* | 10/2008 | Voelkening | G01N 25/08 | 374/27 |
| 2009/0093962 A1* | 4/2009 | Akkurt | G01N 24/081 | 702/11 |
| 2009/0114288 A1* | 5/2009 | Grant | F02D 19/0628 | 137/88 |
| 2010/0174494 A1* | 7/2010 | De Peinder | G01N 21/359 | 702/30 |
| 2010/0204925 A1* | 8/2010 | Albahri | G01N 25/14 | 702/25 |
| 2010/0271019 A1* | 10/2010 | Anand | G01N 24/081 | 324/303 |
| 2010/0305872 A1* | 12/2010 | Abahri | G01N 21/41 | 702/30 |
| 2012/0226425 A1* | 9/2012 | Lunati | F02D 19/0628 | 701/102 |

OTHER PUBLICATIONS

Asadisaghandi J. et al., "Comparative evaluation of back-propagation neural network learning algorithms and empirical correlations for prediction of oil PVT properties in Iran oilfields", Journal of Petroleum Science and Engineering, 78, 2011, pp. 464-475.*

Peinder P. et al., "Partial least squares modeling of combined infrared, 1H NMR and 13C NMR spectra to predict long residue properties of crude oils", Vibrational Spectroscopy, 51, 2009, pp. 205-212.*

Gharbi R. et al., "Universal Neural-Network-Based Model for Estimating the PVT Properties of Crude Oil Systems", Energy & Fuels, 1999, 13, pp. 454-458.*

Ramos P. et al., "Low field 1H NMR relaxometry and multivariate data analysis in crude oil viscosity predietion", Chemometrics and Intelligent Laboratory Systems, 99, 2009, pp. 121-126. (Previously supplied).*

Asadisaghandi J. et al., "Comparative evaluation of back-propagation neural network learning algorithms and empirical correlations for prediction of oil PVT properties in Iran oilfields", Journal of Petroleum Science and Engineering, 78, 2011, pp. 464-475. (Previously supplied).*

Peinder P. et al., "Partial least squares modeling of combined infrared, 1H NMR and 13C NMR spectra to predict long residue properties of crude oils", Vibrational Spectroscopy, 51, 2009, pp. 205-212. (Previously supplied).*

Gharbi R. et al., "Universal Neural-Network-Based Model for Estimating the PVT Properties of Crude Oil Systems", Energy & Fuels, 1999, 13, pp. 454-458. (Previously supplied).*

* cited by examiner

METHOD FOR PREDICTING THE PROPERTIES OF CRUDE OILS BY THE APPLICATION OF NEURAL NETWORKS

This application claims priority from Italian Application No. MI2011A001908, filed Oct. 21, 2011, the subject matter which is incorporated herein by reference in its entirety.

The present invention relates to the field of the study and analysis of materials for determining their physical and chemical properties and in particular a method for predicting the physico-chemical properties of crude oils through the measurement of the NMR (Nuclear Magnetic Resonance) relaxometric properties and analysis of the data through the application of models developed with the use of neural networks.

It is often necessary in the oil industry to know, with a certain accuracy, some of the parameters of crude oils to be able to understand their quality, and which can be useful for a better control of the processes.

The possibility of predicting the properties of a crude oil in short times is a useful commercial and operative analysis instrument.

The methods known in the art mainly consist of analytical techniques of the rheological type such as, for example, physico-chemical methods for measuring the viscosity, the use of thermal or chromatographic gas for obtaining distillation curves and elemental chemical analysis.

The standard analytical techniques currently used require lengthy and costly analyses which represent a considerable burden for their evaluation, especially for technical transformation operations of crude oils. These methods, moreover, can only be effected in laboratories provided with adequate instruments and equipment.

The use of innovative methods based on short-term analyses that can also be easily effected in unequipped sites could represent a valid alternative with a significant advantage in the cognitive and subsequent operative phase of the oil transformation cycle.

Methods based on the use of the NMR technique, used for estimating the physical characteristics of crude oils or heavy residues, are known in the state of the art.

The document entitled "NMR properties of petroleum reservoir fluids" by G. J. Hirasaki, Sho-Wei Lo, Y. Zhang, for example, describes the correlation existing between the average of the relaxation times of the protons of hydrocarbons and the properties of crude oils.

A further known method is described by the document entitled "Characterization of petrochemical products by the application of a mobile NMR instrument" by G. Maddinelli, L. Del Gaudio, U. Cornaro, in which the NMR method is applied for evaluating a series of parameters, in particular the viscosity, on a series of samples coming from a hydrocracking treatment. The method described therein correlates the dynamic viscosity of the products with one of the diffusion measurements of the hydrocarbon molecules.

These methods allow some physical properties such as the dynamic viscosity or the API degree of crude oils to be evaluated.

Another method is described in U.S. Pat. No. 6,477,516 in which the NMR spectrum of a hydrocarbon is divided into regions, each of which is evaluated by quantifying the intensity of the signal; the values thus obtained are applied to a neural network trained to correlate the quantities extracted from the spectrum with the parameters of the hydrocarbon.

Traditional techniques extract the average values of the relaxation times of the protons from the relaxation curves with known methods, such as Carr-Purcell-Meiboom-Gill (CPMG), which allows the measurement of the transversal relaxation time or "spin-spin" (T2). Another known method is l'Inversion-Recovery which allows the measurement of the longitudinal relaxation time or "spin-lattice (T1)"

Once the average values of the relaxation times have been obtained, these are correlated to some physical properties such as, for example, the dynamic viscosity or API degree of crude oils.

The Applicant has surprisingly found that, through a more detailed treatment of the NMR relaxometric curves, it is possible to extract many other parameters. The Applicant has in fact discovered that extremely reliable evaluations can be obtained from NMR relaxometric curves even on physico-chemical parameters forming crude oil, such as for example, asphaltenes, resins and CCR (Conradson Carbon Residue), on elements bound to organic compounds such as sulfur or metals, and on oil distillation curves.

The protons of a molecule of crude oil have the property of being differently oriented depending on the magnetic field to which they are subjected, in particular in relation to the molecular environment to which they belong. The environment is characteristic of each molecule and the physico-chemical characteristics of the molecule itself depend on this.

The Applicant has found that by applying a statistical analysis by means of neural networks to NMR relaxation curves, without fitting processes, much more information on the characteristics of crude oil can be obtained.

A first objective of the present invention is to provide a method for predicting the properties of crude oils by the application of neural networks to NMR relaxation curves, wherein said curves do not undergo any preventive transformation.

A further objective of the present invention is to provide a method for predicting the properties of crude oils by the application of neural networks which avoids complex and laborious physico-chemical analyses that require the use of numerous instrumental techniques.

These objectives, according to the present invention, are achieved by providing a method for predicting the properties of crude oils by the application of neural networks as specified in claim 1.

Further characteristics of the invention are indicated in the dependent claims.

For the purposes of the present invention, the term crude oil indifferently comprises petroleum as it is extracted from reservoirs, or straight run fuel oil, or a mixture of different crude oils.

An object of the present invention relates to a method for predicting the properties of crude oils by the application of neural networks characterized in that it comprises the following phases:
  determining the NMR relaxation curve T2 of an unknown crude oil and converting it to a logarithmic relaxation curve;
  selecting the values of said logarithmic relaxation curve lying on a characterization grid having a distance between subsequent lines ranging from 0.1 ms to 1 ms;
  entering said selected values as input data for a multilayer neural network of the back propagation type, trained and optimized by means of genetic algorithms;
  predicting, by means of said trained and optimized neural network, at least one of the following physico-chemical factors of the unknown crude oil:
  TBP (True Boiling Point) yield
  API degree
  viscosity
  sulfur content acidity
paraffin content
naphthene content
aromatic content
naphthene+2 aromatics content
smoke point
freezing point
cloud point
pour point
cetane index
Nickel content
Vanadium content
asphaltene content
carbon residue content (Conradson Carbon Residue, C.C.R.)

According to a preferred embodiment of the present invention, before predicting the physico-chemical factors of an unknown crude oil, said multilayer neural network of the back propagation type, requires a training and optimization process comprising the following phases:

determining the NMR relaxation curves T2 of at least 5 samples of crude oil;
converting said relaxation curves T2 to logarithmic relaxation curves;
selecting the values of said logarithmic relaxation curves lying on a characterization grid having a distance between subsequent lines ranging from 0.1 ms to 1 ms;
determining, through laboratory analyses, at least one of the following physico-chemical factors of said samples of crude oil:
TBP (True Boiling Point) yield
API degree
viscosity
sulfur content
acidity
paraffin content
naphthene content
aromatic content
naphthene+2 aromatics content
smoke point
freezing point
cloud point
pour point
cetane index
Nickel content
Vanadium content
asphaltene content
carbon residue content (Conradson Carbon Residue, C.C.R.);
entering said selected values of said samples of crude oil as input data for a multilayer neural network of the back propagation type and said physico-chemical factors of said samples of crude oil as output data for said neural network;
using said neural network for correlating said selected values of said samples of crude oil to said physico-chemical factors of said samples of crude oil;
optimizing said neural network by means of genetic algorithms to minimize the absolute error between the quantities predicted through the neural network and the quantities determined by means of laboratory analyses relating to said physico-chemical factors of said samples of crude oil.

In a preferred embodiment of the present invention, said relaxation curve is converted to a logarithmic relaxation curve with base 10 (log 10).

The values used as input for the neural network are selected by intersecting the logarithmic relaxation curves with the lines, having a constant time distance, of a characterization grid.

An excessively short distance between the lines of the grid creates an input overload for the neural network with the consequent risk of overlearning, thus increasing the meaning of the particular case and jeopardizing the predicted value.

Vice versa, an excessive distance between the lines forming said characterization grid leads to a loss of information, jeopardizing the prediction validity of the method.

For the purposes of the present invention, distance values between the lines were selected, which were considered optimum for the prediction purposes of the method. In particular, said distance between the lines can range from 0.1 ms to 1 ms, and is preferably equal to 0.25 ms.

According to a preferred embodiment of the present invention, the average absolute error is considered minimized when the difference between the average of the quantities predicted by means of the present method and the average of the quantities determined experimentally reaches a minimum and constant value during the training and optimization phase.

According to a preferred embodiment of the present invention, the number of samples of crude oil to be analyzed in the training and optimization process may preferably range from 15 to 30.

In a preferred embodiment, said method allows the physico-chemical factors of the unknown crude oil to be predicted according to the scheme defined in Table 1.

TABLE 1

|  |  | CRUDE OIL | GAS C1-C4 | NAPHTHAS | | KEROSENE | GAS OIL | VACUUM DISTILLATE | OILY RESIDUES | |
|---|---|---|---|---|---|---|---|---|---|---|
|  |  |  |  | | | TBP Range: | | | | |
|  |  |  |  | C5-80 | 80-160 | 160-230 | 230-370 | 370-530 | 370+ | 530+ |
| TBP yield | wt % |  | X | X | X | X | X | X | X | X |
| API degree at 60° F. |  | X |  |  |  |  |  |  |  |  |
| Viscosity at 20° C. | cSt | X |  |  |  |  |  |  |  |  |
| Viscosity at 50° C. | VBN |  |  |  |  | X | X | X | X | X |
| Sulfur | wt % | X |  | X | X | X | X | X | X | X |
| Acidity | mgKOH/g | X |  |  |  | X | X | X |  |  |
| Paraffins | % vol |  |  |  | X |  |  |  |  |  |
| Naphthenes | % vol |  |  |  | X |  |  |  |  |  |

TABLE 1-continued

|  |  | CRUDE OIL | GAS C1-C4 | NAPHTHAS | | KEROSENE | GAS OIL | VACUUM DISTILLATE | OILY RESIDUES | |
|---|---|---|---|---|---|---|---|---|---|---|
|  |  |  |  | C5-80 | 80-160 | 160-230 | 230-370 | 370-530 | 370+ | 530+ |
|  |  |  |  | TBP Range: | | | | | | |
| Aromatics | % vol |  |  |  | X |  |  |  |  |  |
| Naphthenes + 2 aromatics |  |  |  |  | X |  |  |  |  |  |
| Smoke point | Mm |  |  |  |  | X |  |  |  |  |
| Freezing point | ° C. |  |  |  |  | X |  |  |  |  |
| Cloud point | ° C. |  |  |  |  |  | X |  |  |  |
| Pour point | ° C. | X |  |  |  |  | X | X | X | X |
| Cetane index |  |  |  |  |  |  | X |  |  |  |
| Nickel | Ppm | X |  |  |  |  |  | X | X | X |
| Vanadium | Ppm | X |  |  |  |  |  | X | X | X |
| Asphaltenes in normal-heptane |  |  |  |  |  |  |  |  |  |  |
| C.C.R. | wt % | X |  |  |  |  |  | X | X | X |

According to a particular embodiment of the present method, said trained and optimized neural network allows the distillation curve of an unknown crude oil to be predicted, alternatively to the prediction of physico-chemical factors of the crude oil.

In this particular embodiment of the present method, the training and optimization process of the multilayer neural network of the back propagation type provides the following phases:
- determining the NMR relaxation curves T2 of at least 5 known sample crude oils;
- converting said relaxation curves T2 to logarithmic relaxation curves;
- selecting the values of said logarithmic relaxation curves lying on a characterization grid having a distance between subsequent lines ranging from 0.1 ms to 1 ms;
- determining, through laboratory analyses, the distillation curves of said sample crude oils;
- entering said selected values of said samples of crude oil as input data for a multilayer neural network of the back propagation type and said distillation curves of said samples of crude oil as output data for said neural network;
- using said neural network for correlating said selected values of said sample crude oils to said distillation curves of said sample crude oils;
- optimizing said neural network by means of genetic algorithms to minimize the absolute error between the quantities predicted through the neural network and the quantities determined by means of laboratory analyses relating to said distillation curves of said sample crude oils.

According to said particular embodiment of the present method, it is possible to predict the distillation curve of crude oil in its various fractions: gas, naphthas, kerosenes, gas oils, vacuum distillates and oily residues.

In particular, during the training and optimization process, the distillation curves of the sample crude oils can be obtained by means of standard methods known to experts in the field.

The present method allows the distillation curve of crude oil to be determined in its various distillation cuts, indicated in Table 2.

TABLE 2

| Distillation cuts | | | | | |
|---|---|---|---|---|---|
| C1 methane | NC4 normal-butane | 100° C. | 180° C. | 270° C. | 370° C. |
| C2 ethane | IC5 Iso-pentane | 120° C. | 210° C. | 290° C. | 400° C. |
| C3 propane | NC5 Normal-pentane | 140° C. | 230° C. | 320° C. | 530° C. |
| IC4 Iso-butane |  | 80° C. | 160° C. | 250° C. | 350° C. | 550° C. |

According to the present invention, the number of values defined and selected intersecting the relaxation curves and characterization grids described in the present invention, is a finite number never higher than 10,000.

With reference to Table 2, the distillation fraction or cut can be identified according to the nature of the compound, for example C4 i.e. butane, or the distillation temperature, for example 120° C.

Further characteristics and advantages of the method for predicting the properties of crude oils by the application of neural networks will appear more evident from the following description of an illustrative and non-limiting embodiment, with reference to the enclosed drawings, in which.

Figure 1:
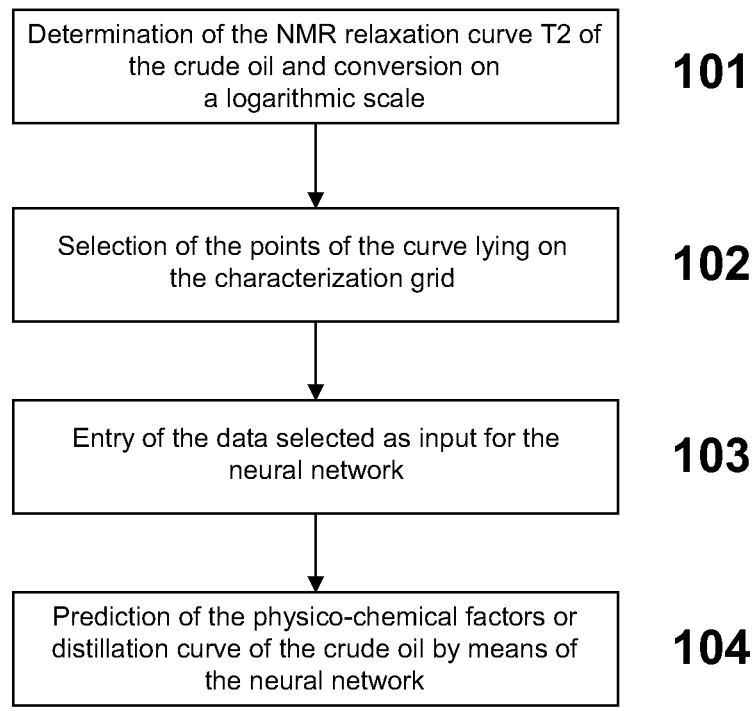
FIG. 1 illustrates a block scheme indicating the main phases of the method according to the present invention.

With reference to FIG. 1, this illustrates a preferred prediction method, comprising a first phase for determining the NMR relaxation curve T2 (phase 101) by means of techniques known in the state of the art.

Figure 4:
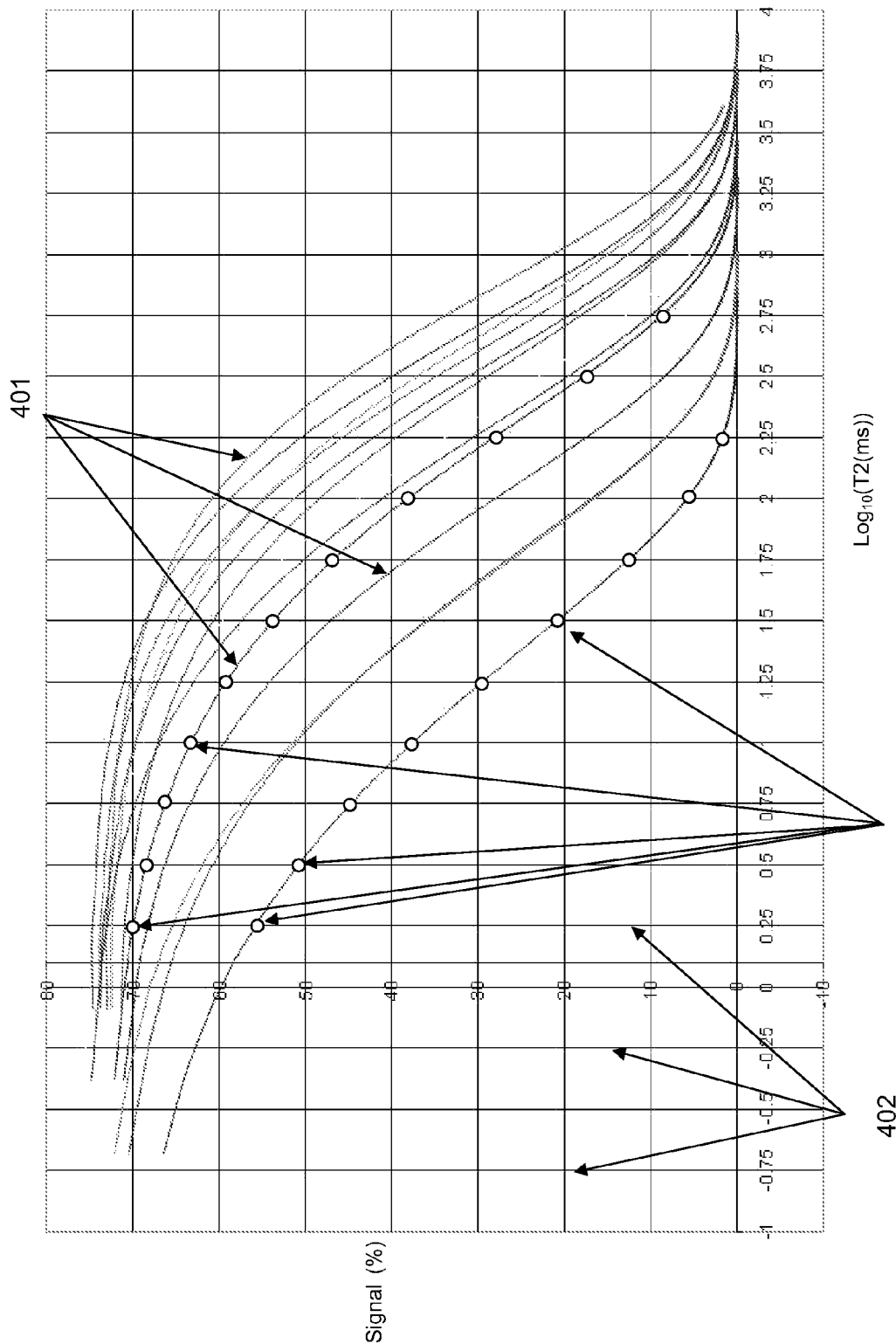
FIG. 4 illustrates the logarithmic relaxation curve with base 10 of some sample crude oils and a characterization grid with vertical lines.

With further reference to FIG. 4, said NMR relaxation curve T2 is subsequently converted into a logarithmic relaxation curve (401) and intersected with a characterization grid (402).

Figure 3:
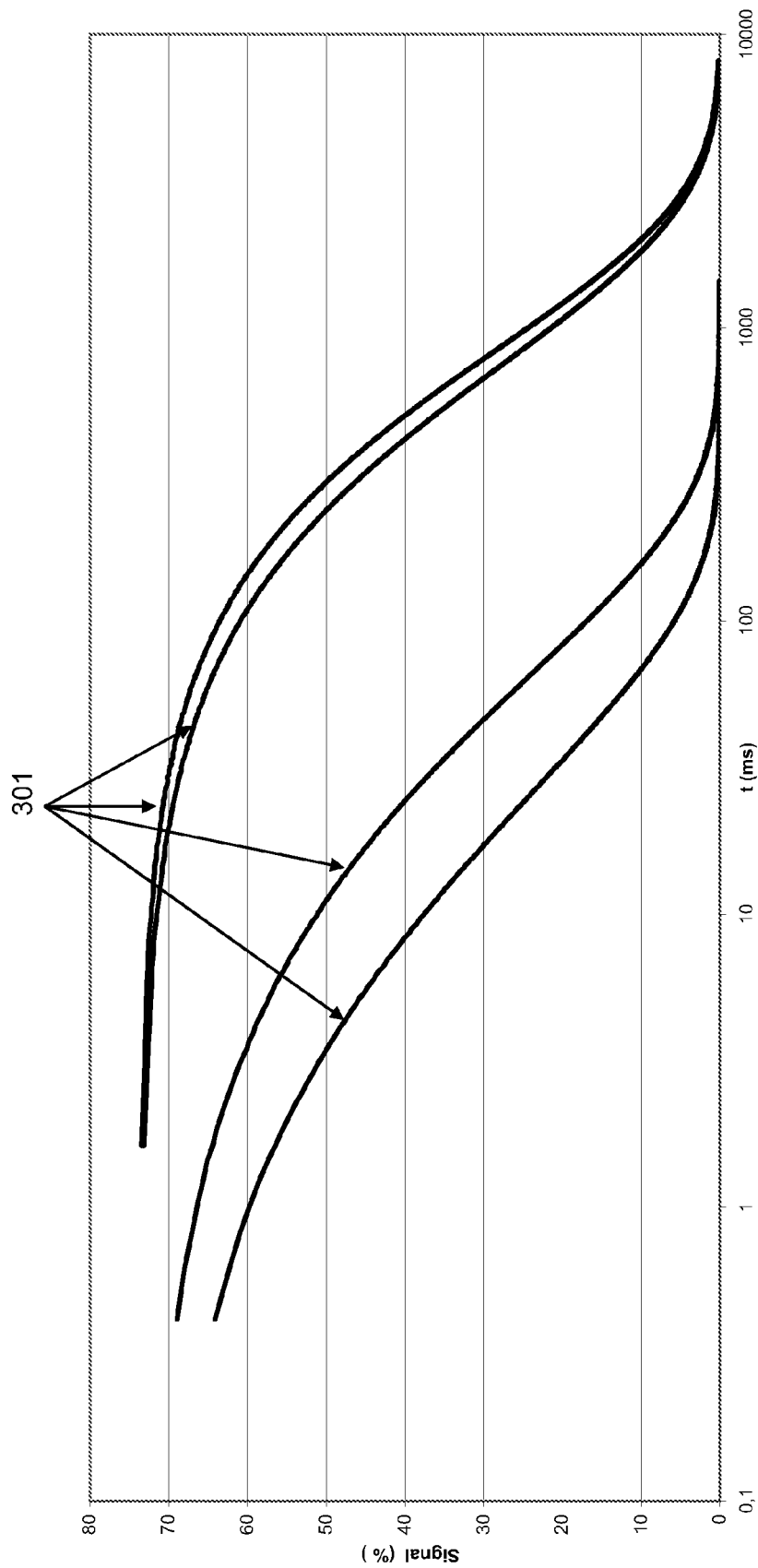
FIG. 3 illustrates the relaxation curve T2 of some sample crude oils.

FIG. 3 shows some illustrative NMR relaxation curves T2 (301), in which each curve represents the time required for the transversal magnetization to fall with respect to the initial value.

In relation to the preselected time intervals for defining the amplitude of the meshes of the characterization grid (402), the points (403) of the logarithmic curve (401) to be selected (phase 102) for the subsequent phase of feeding data to the neural network (phase 103), are identified.

With particular reference to FIG. 4, the time is represented on the axis of the abscissa and the points (403) of the logarithmic relaxation curve (401) to be selected, are those that intersect the vertical lines of the characterization grid (402).

Each of these points selected represents the signal that can be obtained from the logarithmic curve T2 in correspondence with a precise time value.

The time values are selected at regular time intervals and range from 0.1 ms to 1 ms.

The values of the logarithmic relaxation curve selected are subsequently used as input for a multilayer neural network of the back propagation type (phase 103), for predicting the physico-chemical factors, or alternatively the distillation curve, of a crude oil (phase 104).

Figure 2:
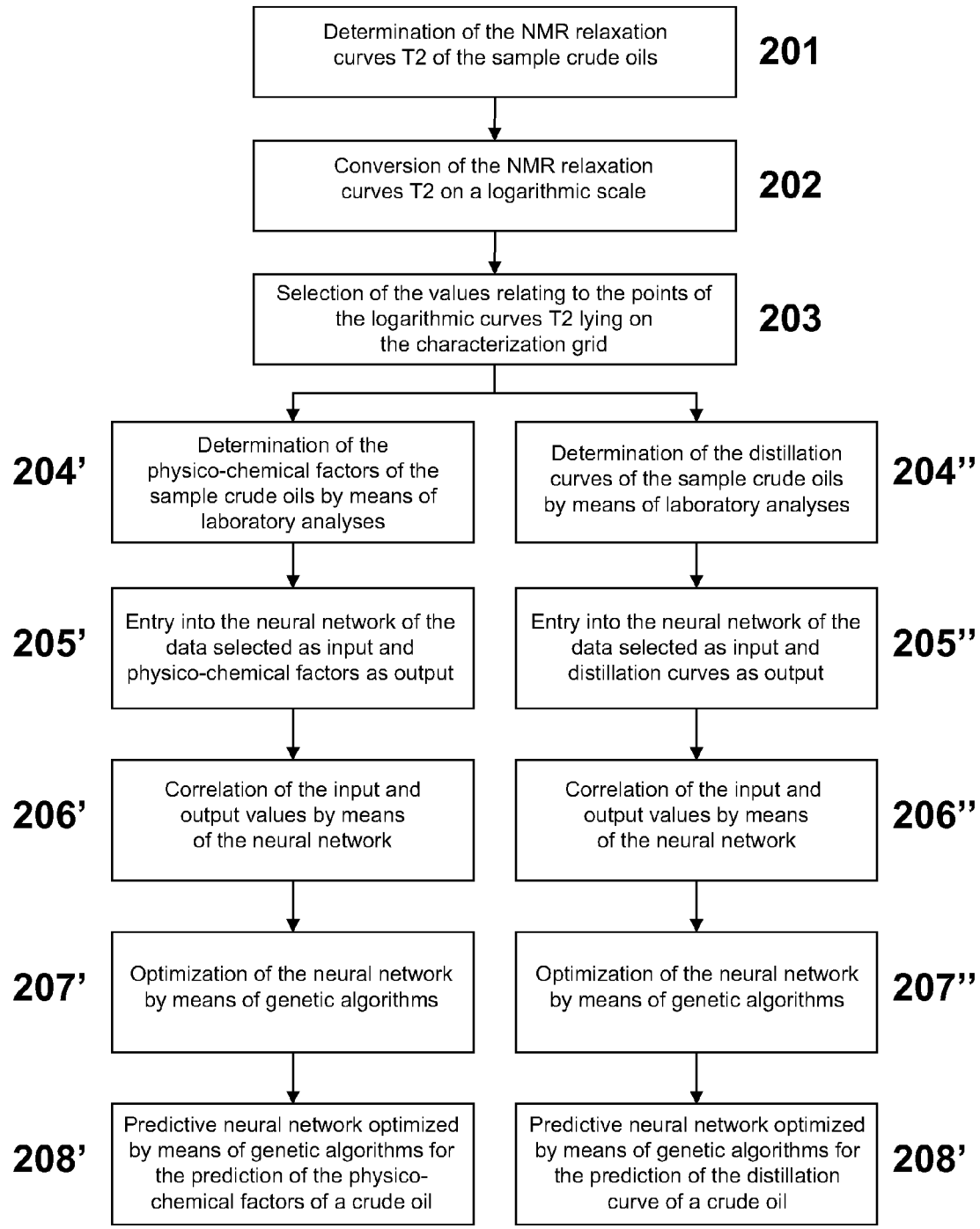
FIG. 2 illustrates a block scheme indicating the main phases of the training and optimization process of the neural network according to the present invention.

Said neural network is trained and optimized, according to the process represented by the diagram in FIG. 2.

In particular, before being used for predicting unknown crude oils, said neural network requires a training and optimization process effected on known samples crude oils.

With reference to FIG. 2, the NMR relaxation curves T2 are determined, of a certain number of sample crude oils, preferably higher than 5 (phase 201).

Said NMR relaxation curves T2 are then converted to the equivalent logarithmic relaxation curves (phase 202).

The signal values corresponding to precise time intervals of these logarithmic curves are then selected (phase 203). Said time intervals, represented in FIG. 4 as vertical lines of a characterization grid, are established a priori and range from 0.1 ms to 1 ms.

The same sample crude oils used for obtaining the NMR relaxation curves T2 are subjected to standard laboratory analyses, known in the art, to identify some of the physico-chemical parameters of the crude oil (phase 204') or alternatively to determine the distillation curve of the crude oil (phase 204").

Various neural networks are constructed, depending on the required parameter, i.e. physico-chemical factors or distillation curve.

In the former case (phase 204'), the values of the following physico-chemical factors are obtained by laboratory analyses for each sample of crude oil analyzed:
TBP (True Boiling Point) yield
API degree
viscosity
sulfur content
acidity
paraffin content
naphthene content
aromatic content
naphthene+2 aromatics content
smoke point
freezing point
cloud point
pour point
cetane index
Nickel content
Vanadium content
asphaltene content
carbon residue content (Conradson Carbon Residue, C.C.R.).

These factors are entered as output for the neural calculation, whereas the selected values of the logarithmic relaxation curves are entered as input (phase 205').

Said neural network is subsequently trained to correlate said input to said output (phase 206') and optimized by means of genetic algorithms to minimize the absolute error between the predicted values and the values obtained by means of laboratory analyses (phase 207').

Once the absolute error has been minimized, the neural network is ready (phase 208') for predicting the physico-chemical factors of an unknown crude oil, as envisaged by phase 104 of the diagram in FIG. 1.

Alternatively, said neural network can be developed in order to correlate the selected values of the logarithmic relaxation curves to the distillation curves of the relative sample crude oils.

In this case, the selected values of the relaxation curves are used as input and the distillation curves of the samples of crude oils as output of the neural network (phase 205").

Said neural network is subsequently trained to correlate said input to said output (phase 206") and optimized by means of genetic algorithms to minimize the absolute error between the predicted values and the values obtained by means of laboratory analyses (phase 207").

Once the absolute error has been minimized, the neural network is ready (phase 208") for predicting the distillation curve of an unknown crude oil, as envisaged by phase 104 of the diagram in FIG. 1.

According to the present invention, the method thus defined allows the most representative physico-chemical factors of crude oil to be predicted in rapid times and without onerous laboratory structures, or alternatively the distillation curve of crude oil with an approximation degree considered acceptable.

EXAMPLE 1

A sample of 16 crude oils of different origins was analyzed in the laboratory with respect to its physico-chemical properties. The NMR relaxation curve T2 of each crude oil was determined.

In particular, the crude oils indicated in Table 3 were analyzed, described in terms of origin, API degree and sulfur content.

TABLE 3

| Origin | API | Sulfur [wt %] |
|---|---|---|
| IRAN | 19.0 | 2.67 |
| IRAN | 20.5 | 3.99 |
| EGYPT | 24.8 | 2.53 |
| VENEZUELA | 24.9 | 2.41 |
| LIBYA | 26.0 | 1.82 |
| IRAQ | 29.2 | 2.96 |
| NIGERIA | 29.5 | 0.26 |
| IRAQ | 29.8 | 2.87 |

TABLE 3-continued

| Origin | API | Sulfur [wt %] |
|---|---|---|
| CONGO | 31.8 | 0.10 |
| CONGO | 32.2 | 0.11 |
| SAUDI ARABIA | 33.0 | 1.88 |
| KAZAKHSTAN | 34.4 | 0.28 |
| LIBYA | 36.8 | 0.41 |
| CONGO | 40.2 | 0.04 |
| LIBYA | 42.4 | 0.22 |
| KAZAKHSTAN | 43.3 | 0.54 |

Some of the physico-chemical characteristics of the sample crude oils were then analyzed. Table 4 indicates the average values of the variability ranges of the physico-chemical characteristics taken into consideration.

TABLE 4

| Values | API | Sulfur [wt %] | Viscosity at 20° C. [cSt] | Pour point, [° C.] | Acidity [mg KOH/g] | Ni content, [ppm] | V content [ppm] | Charact. factor UOP | Asphaltenes, in n-C7 [wt %] | Conradson Carbon Residue CCR [wt %] | Yield of 370+° C. fraction [wt %] |
|---|---|---|---|---|---|---|---|---|---|---|---|
| MIN | 19.0 | 0.04 | 3.24 | −33 | 0.07 | 1.8 | 0.6 | 11.4 | 0.11 | 0.85 | 26.6 |
| MAX | 43.3 | 3.99 | 918.35 | 21 | 1.18 | 63.6 | 116.8 | 12.3 | 8.61 | 12.83 | 67.7 |
| Average | 31.1 | 1.44 | 100.46 | −1 | 0.31 | 18.7 | 50.2 | 11.9 | 2.46 | 5.13 | 48.6 |

The relaxation curves T2 of the crude oils analyzed were converted into the corresponding logarithmic relaxation curves (log 10), as illustrated in FIG. 4.

With reference to FIG. 4, the values (403) lying on a characterization grid were selected (input data for the neural calculation).

The characterization grid was identified so as to reduce the calculation parameters, without however losing the important information contained in the same data.

The values of the curve having as coordinates in the abscissa the values expressed in Table 5, were then selected.

TABLE 5

| axis X Log10 (T2)= | | | | | | | | | | | | |
|---|---|---|---|---|---|---|---|---|---|---|---|---|
| 0.25 | 0.5 | 0.75 | 1 | 1.25 | 1.5 | 1.75 | 2 | 2.25 | 2.5 | 2.75 | 3 | 3.25 |

The parameters selected were then used as input data for identifying a correlation between the NMR relaxation curves T2 and the properties of the crude oils and their fractions.

In order to identify the correlation between the factors, non-linear algorithms were used, in particular multilayer neural networks of the back propagation type, optimized with genetic algorithms.

Table 6 indicates the physico-chemical characteristics (output data) of the crude oils and their fractions.

TABLE 6

| | | Crude oil | Gas C1-C4 | Naphthas | | Kerosene | Gas oil | Vacuum distillate | Oily residues | |
|---|---|---|---|---|---|---|---|---|---|---|
| | | | | | | TBP Range: | | | | |
| | | | | C5-80 | 80-160 | 160-230 | 230-370 | 370-530 | 370+ | 530+ |
| API degree at 60° F. | | X | | | | | | | | |
| Viscosity at 20° C. | cSt | X | | | | | | | | |
| Viscosity at 50° C. | VBN | | | | | X | X | X | X | X |
| Sulfur | % peso | X | | X | X | X | X | X | X | X |
| Acidity | mgKOH/g | X | | | | X | X | X | | |
| Paraffins | % vol | | | | X | | | | | |
| Naphthenes | % vol | | | | X | | | | | |
| Aromatics | % vol | | | | X | | | | | |

TABLE 6-continued

| | | Crude oil | Gas C1-C4 | Naphthas C5-80 | Naphthas 80-160 | Kerosene TBP Range: 160-230 | Gas oil 230-370 | Vacuum distillate 370-530 | Oily residues 370+ | Oily residues 530+ |
|---|---|---|---|---|---|---|---|---|---|---|
| Naphthenes + 2 aromatics | | | | | X | | | | | |
| Smoke point | Mm | | | | | X | | | | |
| Freezing point | °C. | | | | | X | | | | |
| Cloud point | °C. | | | | | | X | | | |
| Pour point | °C. | X | | | | | X | X | X | X |
| Cetane index | | | | | | | X | | | |
| Nickel | Ppm | X | | | | | | X | X | X |
| Vanadium | Ppm | X | | | | | | X | X | X |
| Asphaltenes in normal-heptane | | | | | | | | | | |
| C.C.R. | wt % | X | | | | | | X | X | X |

Table 7 indicates some correlation factors for the parameters predicted, the absolute error (minimum, maximum and average) obtained from a comparison between the experimental values and the values calculated with the neural network.

TABLE 7

| | Average standard deviation | Error max | Error min | Error average |
|---|---|---|---|---|
| API | 0.9851 | 2.80 | 0.02 | 0.84 |
| Sulfur [wt %] | 0.9913 | 0.36 | 0.01 | 0.14 |
| Viscosity at 20° C. [cSt] | 0.9829 | 44.82 | 1.35 | 11.60 |
| TAN | 0.9258 | 0.20 | 0.03 | 0.09 |
| Ni content [ppm] | 0.9440 | 22.33 | 0.92 | 4.98 |
| V content [ppm] | 0.9771 | 20.88 | 0.23 | 5.51 |
| Asphaltenes in n-C7 [wt %] | 0.9789 | 1.38 | 0.01 | 0.40 |
| CCR, | 0.9734 | 1.62 | 0.01 | 0.60 |
| C5-80 cut [wt %] | 0.9145 | 2.33 | 0.02 | 0.57 |
| 80-160 cut [wt %] | 0.9199 | 3.70 | 0.19 | 1.13 |
| 160-230 cut [wt %] | 0.9268 | 2.08 | 0.05 | 0.80 |
| sulfur in 160-230 cut [wt %] | 0.9191 | 0.21 | 0.00 | 0.05 |
| 230-370 cut [wt %] | 0.6509 | 9.79 | 0.01 | 2.24 |
| sulfur in 230-370 cut [wt %] | 0.9809 | 0.35 | 0.02 | 0.13 |
| 370-530 cut [wt %] | 0.8770 | 2.37 | 0.01 | 1.04 |
| sulfur in 370-530 cut [wt %] | 0.9818 | 0.49 | 0.02 | 0.21 |
| CCR in 370-530 cut [wt %] | 0.9269 | 0.15 | 0.02 | 0.07 |
| 530+ cut [wt %] | 0.9214 | 11.29 | 0.09 | 3.00 |
| viscosity at 50° C. in 530+ cut [VBN] | 0.9461 | 2.39 | 0.10 | 0.87 |
| sulfur in 530+ cut [wt %] | 0.9820 | 0.76 | 0.04 | 0.36 |

Figure 5:
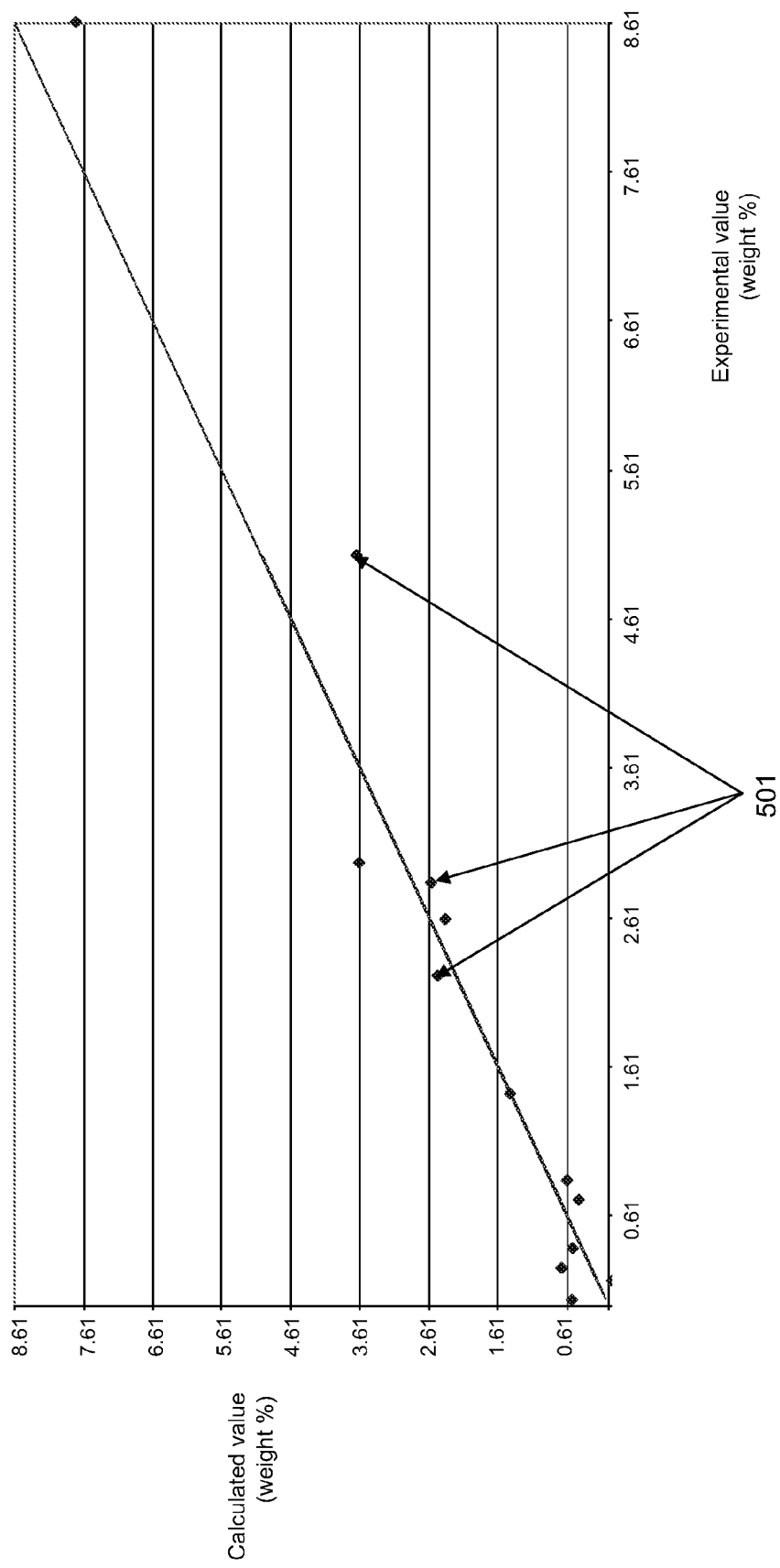
FIG. 5 illustrates a graphic comparison between the predicted values relating to the asphaltene content in n-C7, and those obtained with laboratory analyses, for various sample crude oils.

FIG. 5 shows a graph relating to the prediction of the content of n-C7 asphaltenes, which indicates a good correlation between the predicted values and the calculated values.

FIG. 5 shows a graphic representation of the values (501) obtained by means of laboratory analyses (abscissa), relating to the content of n-C7 asphaltenes intersected with the corresponding predicted values by means of the trained and optimized neural network.

EXAMPLE 2

The same sample of 16 crude oils used for Example 1 was characterized with respect to the NMR relaxation curve T2 and the atmospheric and vacuum distillation curve, according to the standard methods ASTM D2892 and ASTM D1160.

Table 8 indicates the temperatures to which the values of the cumulative yields used in the Example correspond.

TABLE 8

| | | Distillation cuts | | | | |
|---|---|---|---|---|---|---|
| C1 methane | NC4 normal-butane | 100° C. | 180° C. | 270° C. | 370° C. | |
| C2 ethane | IC5 Iso-pentane | 120° C. | 210° C. | 290° C. | 400° C. | |
| C3 propane | NC5 Normal-pentane | 140° C. | 230° C. | 320° C. | 530° C. | |
| IC4 Iso-butane | 80° C. | 160° C. | 250° C. | 350° C. | 550° C. | |

The input parameters for the neural algorithms were identified as described in Example 1 and were used analogously for identifying a correlation between the NMR relaxation curves T2 and the distillation curves of the crude oils, obtained by means of standard laboratory analyses, known in the art.

Table 9 indicates the correlation factors for the parameters predicted and the absolute error (minimum, maximum and average) between the experimental values and the values calculated with the neural network, from which a good correspondence is revealed, above all for the heavy fractions.

TABLE 9

Distillation curve of the crude oil

| cuts | Average standard deviation | Absolute error max | Absolute error Min | Absolute error average |
|---|---|---|---|---|
| C1 | n.a. | 0.00 | 0.00 | 0.00 |
| C2 | 0.4399 | 0.05 | 0.00 | 0.01 |
| C3 | 0.4247 | 0.14 | 0.02 | 0.07 |
| IC4 | 0.7756 | 0.21 | 0.03 | 0.11 |
| NC4 | 0.8924 | 0.62 | 0.01 | 0.22 |
| IC5 | 0.9368 | 0.81 | 0.01 | 0.27 |
| NC5 | 0.9380 | 1.14 | 0.01 | 0.38 |
| 80° C. | 0.9479 | 1.50 | 0.03 | 0.59 |
| 100° C. | 0.9559 | 2.33 | 0.10 | 0.71 |
| 120° C. | 0.9628 | 2.69 | 0.06 | 0.82 |
| 140° C. | 0.9646 | 3.32 | 0.09 | 1.05 |
| 160° C. | 0.9561 | 4.28 | 0.09 | 1.38 |
| 180° C. | 0.9555 | 4.58 | 0.18 | 1.64 |
| 210° C. | 0.9587 | 4.68 | 0.32 | 1.90 |
| 230° C. | 0.9616 | 5.07 | 0.62 | 1.97 |
| 250° C. | 0.9660 | 5.41 | 0.47 | 1.94 |
| 270° C. | 0.9689 | 5.31 | 0.01 | 1.89 |
| 290° C. | 0.9658 | 5.37 | 0.29 | 2.09 |
| 320° C. | 0.9587 | 6.33 | 0.05 | 2.38 |
| 350° C. | 0.9526 | 6.42 | 0.46 | 2.66 |
| 370° C. | 0.9505 | 7.01 | 0.43 | 2.77 |
| 400° C. | 0.9508 | 7.47 | 0.27 | 2.76 |
| 530° C. | 0.9512 | 8.68 | 0.45 | 2.57 |
| 550° C. | 0.9461 | 7.50 | 0.78 | 2.53 |

The invention claimed is:

1. A method for predicting the properties of crude oils by the application of neural networks characterized in that it comprises the following phases:
   determining a T2 NMR (Nuclear Magnetic Resonance) relaxation curve of an unknown crude oil and converting it to a logarithmic relaxation curve;
   selecting values of said logarithmic relaxation curve lying on a characterization grid having a distance between subsequent lines ranging from 0.1 ms to 1 ms, wherein the values are selected by intersecting said logarithmic relaxation curve with lines, having a constant time distance, of the characterization grid;
   entering said selected values as input data for a multilayer neural network of the back propagation type, trained and optimized by means of genetic algorithms;
   predicting, by means of said trained and optimized neural network, at least one of the following physico-chemical factors of the unknown crude oil:
   TBP (True Boiling Point) yield,
   API (American Petroleum Institute) degree,
   viscosity,
   sulfur content,
   acidity,
   paraffin content,
   naphthene content,
   aromatic content,
   naphthene+2 aromatic content,
   smoke point,
   freezing point,
   cloud point,
   pour point,
   cetane index,
   Nickel content,
   Vanadium content,
   asphaltene content, or
   carbonaceous residue content,
   or predicting, by means of said trained and optimized neural network, the distillation curve of an unknown crude oil.

2. The method according to claim 1, wherein, before predicting the physico-chemical factors of an unknown crude oil, said multilayer neural network of the back propagation type, requires a training and optimization process comprising the following phases:
   determining the T2 NMR relaxation curves of at least 5 crude oil samples;
   converting said T2 relaxation curves to logarithmic relaxation curves;
   selecting the values of said logarithmic relaxation curves lying on a characterization grid having a distance between subsequent lines ranging from 0.1 ms to 1 ms;
   determining, through laboratory analyses, at least one of the following physico-chemical factors of said crude oil samples:
   TBP yield,
   API degree,
   viscosity,
   sulfur content,
   acidity,
   paraffin content,
   naphthene content,
   aromatic content,
   naphthene+2 aromatic content,
   smoke point,
   freezing point,
   cloud point,
   pour point,
   cetane index,
   Nickel content,
   Vanadium content,
   asphaltene content, or
   carbonaceous residue content;
   entering said selected values of said crude oil samples as input data for a multilayer neural network of the back propagation type and said physico-chemical factors of said crude oil samples as output data for said neural network;
   using said neural network for correlating said selected values of said crude oil samples to said physico-chemical factors of said crude oil samples;
   optimizing said neural network by means of genetic algorithms to minimize the absolute error between the quantities predicted through the neural network and the quantities determined by means of laboratory analyses relating to said physico-chemical factors of said crude oil samples.

3. The method according to claim 1, wherein, before predicting the distillation curve of an unknown crude oil, said multilayer neural network of the back propagation type requires a training and optimization process comprising the following phases:
   determining the T2 NMR relaxation curves of at least 5 known crude oil samples;
   converting said T2 relaxation curves to logarithmic relaxation curves;
   selecting the values of said logarithmic relaxation curves lying on a characterization grid having a distance between subsequent lines ranging from 0.1 ms to 1 ms;
   determining, through laboratory analyses, the distillation curves of said crude oil samples;
   entering said selected values of said crude oil samples as input data for a multilayer neural network of the back propagation type and said distillation curves of said crude oil samples as output data for said neural network;

using said neural network for correlating said selected values of said crude oil samples to said distillation curves of said crude oil samples;

optimizing said neural network by means of genetic algorithms to minimize the absolute error between the quantities predicted through the neural network and the quantities determined by means of laboratory analyses relating to said distillation curves of said crude oil samples.

4. The method according to claim 1, wherein said method allows the distillation curve of the crude oil to be predicted in its various fractions: gas, naphthas, kerosenes, gas oils, vacuum distillates and oily residues.

5. The method according to claim 1, wherein said relaxation curve is converted to a logarithmic relaxation curve with base 10 ($\log_{10}$).

6. The method according to claim 1, wherein the distance between the lines is equal to 0.25 ms.

7. The method according to claim 2, wherein the number of crude oil samples to be analyzed in the training and optimization process ranges from 15 to 30.

* * * * *